United States Patent [19]

Blanchette et al.

[11] Patent Number: 5,711,945
[45] Date of Patent: Jan. 27, 1998

[54] PITCH DEGRADATION WITH PSEUDOMONAS FLUORESCENS

[75] Inventors: Robert A. Blanchette, Shoreview; Todd A. Burnes, St. Paul, both of Minn.; Roberta L. Farrell, Groton, Mass.

[73] Assignee: Regents of the University of Minnesota, Minneapolis, Minn.

[21] Appl. No.: 438,823

[22] Filed: May 11, 1995

[51] Int. Cl.$^6$ .............................. A01N 63/00; C12N 1/20
[52] U.S. Cl. ................................. 424/93.47; 435/253.3; 435/262; 162/174; 162/199
[58] Field of Search ................... 435/262, 252.1, 435/253.3; 162/174, 199; 424/93.47

[56] References Cited

FOREIGN PATENT DOCUMENTS

WO9213130  8/1992  WIPO .
WO9421854  9/1994  WIPO .

OTHER PUBLICATIONS

Biological Degradation of Wood, Blanchette, et al., Dept. of Plant Pathology, U. of Minnesota, Swedish U. of Agriculture Sciences, Dept. of Forest Products, 1990, American Chemical Society, pp. 141–174.

Wood; Decat, pests and protection, Eaton, R.A., et al., Chapter 6, "Bacterial attack", pp. 146–159.

Microbial Degradation of Diterpenic Acids, Biellmann, J.F., et al., Chemical Soc. London, Chemical Communications, 1968, pp. 168–169.

The Bacterial Transformation of Abietic Acid, Cross, B.E., et al., Dept. of Organic Chemistry, U. of Leeds, Biochem. J. (1968) 108, pp. 303–310.

Hydroxylation of Dehydroabietic Acid by Fomes annosus, Ekman, R., et al., Acta Chemica Scandinavica B 33 (1979), pp. 76–78.

Modified Resin Acids In The Reaction Zone Of Fomes annosus–Affected Sapwood of Norway Spruce, Ekman, R., Acta Academiae Aboensis, Ser. B, vol. 39, No. 6, 1979, pp. 1–7.

A Simple Method For The Detection Of Lipolytic Activity Of Micro-Organisms And Some Observations On The Influence Of The Contact Between Cells And Fatty Substrates, Laboratory of Microbiology, Amsterdam, Holland & Dept. of Biochemistry, Madrid, Spain, Sierra, G., 1956, pp. 15–22.

Studies on the production of lipase from recombinant Staphylococcus carnosus, Applied Microbiology & Biotechnology, Springer–Verlag, 1991, 35: 10–13.

Temperature regulation of lipase secretion by Pseudomonas fluorescens Strain MFO, Merieau, A., et al., Applied Microbiology & Biotechnology, Springer–Verlag, 1993, 39:104–109.

Screening for lipase–producing microorganisms with a continuous cultivation system; Lie, E., et al., Applied Microbiology & Biotechnology, Springer–Verlag, 1991, 35:19–20.

Degradation Bacterienne De L'Acide Dehydroabietique Par Un Pseudomonas et Une Alcaligenes, Biellmann, J.F., et al., Tetrahedron, vol. 29, pp. 1237–1241, Pergamon Press, 1973 (Abstract).

Degradation Bacterienne De L'Acide Dehydroabietique Par Flavobacterium Resinovorum, Biellmann, J.F., et al., Tetrahedron, vol. 29, pp. 1227–1236, Pergamon Press, 1973 (Abstract).

No. 269–Degradation microbienne de l'acide dehydroabietique, Biellmann, J.F., et al., Bulletin De La Societe Chimique De France, 1971, No. 5, pp. 1676–1686.

Observations nouvelles concernant la nutrition carbonee de Bacteries retinolytiques, Raynaud, M., et al., Seance Du 15 Janvier, 1966, pp. 371–375.

Les Bacteries Retinolytiques, Raynaud, et al., Annales De L'Institut Pasteur, T. 115, Oct. 1968, No. 4, pp. 731–744.

Microbiologie Du Sol.–Observations concernant la presence de Bacteries retinolytiques dans divers sols du territoire francais, Faure–Raynaud, M., et al., C.R. Acad. Sc. Paris, t. 268 (16 Jun. 1969), pp. 2971–2974.

"Permeability Changes Induced in Three Western Conifers By Selective Bacterial Inoculation", Johnson, B.R., Forest Products Laboratory, Wood & Fiber, vol. 11, No. 1, 1979, pp. 10–21.

"Using Simons Stain to Predict Energy Savings During Biomechanical Pulping", Akhtar, M., et al., Wood & Fiber Science, 27(3), 1995, pp. 258–264.

Primary Examiner—Blaine Lankford

[57] ABSTRACT

The bacteria Pseudomonas fluorescens and Xanthomonas campestris are useful in reducing the pitch content of pulps and pulpwoods used in making cellulosic products. Such bacteria are also useful in reducing the color staining by staining fungi of structural wood by inoculating the structural wood or log sources from which it is to be cut.

23 Claims, No Drawings

PITCH DEGRADATION WITH *PSEUDOMONAS FLUORESCENS*

The present invention relates generally to reducing the pitch content of materials used for manufacturing cellulosic products, and particularly to the microbial inoculation of wood substrates to effect such pitch degradation.

BACKGROUND

Wood is a complex material composed of cellulose, hemicellulose, lignin and wood extractives or a resinous material commonly called "pitch", "resin" or "wood resin". The composition of pitch has been studied and previously reported widely in the literature, e.g., *Wood Extractives and Their Significance to the Pulp and Paper Industry*, Chapter 10 "Wood Resins" by D. B. Mutton; W. E. Hillis, Ed, Academic Press, N.Y. (1962).

In the production of products from wood pulps, the presence of pitch is undesirable as due to its viscosity and tenacity it frequently forms deposits which are difficult to remove, causing relatively frequent and lengthy periods of down-time for cleaning, as resins tend to accumulate as deposits on strainer plates, filters, and throughout paper processing apparatus. It is well-known that pitch may also discolor pulp and paper formed therefrom if allowed to accumulate too long before cleaning. Other drawbacks are known in the art, e.g. waste stream pollution. In Nilsson, et al., U.S. Pat. No. 3,486,969, it is disclosed that certain fungi may be used to inoculate wood chips to reduce the resin content therein and the pulp therefrom while minimizing degradation of the other components of the wood, especially cellulose and hemicellulose. The species of fungi therein disclosed, however, are apparently all mold type or surface forming fungi which, when discoloring the wood, produce essentially a surface or superficial stain which may be readily planed off (see J. S. Boyce, *Forest Pathology*, 3rd. Ed., 1961, McGraw-Hill Book Co. at pp. 493–512, especially 496–497). Such fungi have failed to achieve practical success to our knowledge.

In our published European patent application EP 03 87 187 A2 (based on U.S. patent application Ser. No. 310,814, filed 13 Feb. 1989) there are described the application of certain wood-penetrating fungi generally classed as *Ascomycetes* or *Deuteromycetes* to pulpwoods and pulps to reduce the pitch content thereof. Similarly useful wood-penetrating fungal derivatives are also disclosed in our published European patent application EP 04 70 929 A2 (based on U.S. patent applications having Ser. No. 560,521, filed Jul. 31, 1990 and copending Ser. No. 657,581, filed Feb. 19, 1991).

In our copending U.S. patent application Ser. No. 889,796, filed Jun. 17, 1992, there are described other strain derivatives of a preferred wood-penetrating fungus *Ophiostoma piliferum* which exhibit very good pitch degrading and aggressive growth characteristics while growing white or colorless on treated substrates.

A succession of preferred and improved wood-penetrating strains of *O. piliferum* as above-described have demonstrated commercial capability and have achieved commercial success. In addition to substantial savings from pitch reduction, early indications of greater paper strength (translating into faster machine speeds) have been confirmed and there are further indications of greater pulping efficiency, particularly, for example, when used on substrates for chemical pulping, probably due to the ability of the fungus to substantially open up resin ducts and ray parenchyma cells. The ability of such fungi to be useful practically is in part attributed to the ability of the fungi to grow competitively on non-sterile substrates and not be excluded or dominated by other fungi or organisms which naturally infect wood sources.

Certain white-rot fungi have been also found useful in degrading pitch in pulps and pulpwoods, and particularly in non-sterile substrates, as described in U.S. Ser. No. 08/034,443, filed Mar. 19, 1993.

Definition of Terms

By the terms "resin" or "pitch" (which are used interchangeably) is meant that complex mixture of hydrophobic substances in wood, commonly known as pitch, which are soluble in neutral organic solvents, such as methylene chloride, diethyl ether, benzyl alcohol and the like. These include the terpenes, the diterpene ("resin") acids, fatty acids and esters, glycerides and waxes as well as alcohols, hydrocarbons and other compounds associated therewith. The standard TAPPI extraction analysis using dichlorobenzene or ethanol/toluene will suffice to measure the reduction in resins for the purposes described by the inventors herein.

Resin or pitch is a significant constituent of both softwoods, such as southern pine, spruce and other conifers and hardwoods, such as *Betula* and *Populus*, and it may comprise as much as 4% weight percent or even more of the feed sent to mechanical or chemical pulping processes, generally 1.5 to 4.0% for most woods used for pulping. Softwoods generally contain more resin than hardwoods, with pines having among the highest resin content among softwoods. In hardwoods, resin is located primarily in the ray parenchyma cells which form much of the fiber fraction when wood is pulped. In softwoods, resin is contained in both the ray parenchyma cells and also in resin ducts.

The term "pulpwood" as used herein means any harvested (cut down) form of a tree material used in making paper, cardboard or other cellulosic products such as viscose, but prior to pulping, and includes such forms as timber, logs, wood chips, sawdust and the like. The term "refined pulpwood" means a pulpwood resulting from the application of mechanical and/or shearing forces to whole pulpwood forms such as logs to obtain a multiplicity of high surface area, small pieces, such as wood chips and sawdust, which are introducible into a pulping process. The invention may also be applied to lignin-containing cellulosic materials classifiable as pulps which have yet to undergo sufficient treatment to significantly reduce its lignin content (and liberate contained pitch), in particular pulp which still retains 60% or more of its original lignin content, such as first stage mechanical pulp.

By the term "inoculum" and the like as used herein is meant any microbial material which is sufficiently viable to result in its growth, when applied to a substrate. Typical inocula include cultures or cell preparations obtained from such cultures, including spores, desirably from a biologically pure culture. An inoculum form may be provided by culturing the organisms in any of several conventional ways. Solid or liquid culturing media may be used as desired or required.

Therefore, a need exists for improved degradation of pulp and pulpwoods which overcomes those disadvantages associated with the methods described above.

SUMMARY OF THE INVENTION

According to the present invention there is provided a method for reducing the resin component of pulpwoods and incompletely refined pulps. The method comprises the steps of applying to the pulpwood or pulp substrate a bacterial inoculum of at least one of the species selected from the group comprising *Pseudomonas fluorescens* and *Xanthomonas campestris* and maintaining the substrate under conditions which allow bacterial growth for a time sufficient to effect a reduction in the resin component of the substrate by the bacteria.

An advantage of the present invention is a method that is effective to reduce the resin content in a variety of pulps and pulpwoods.

Another advantage is the practical efficacy of the present method under non-sterile conditions which reflect those encountered during actual use.

A further advantage of the present method is the use of a bacterial inoculum which affords a greater flexibility of operating parameters than for organisms used in existing methods, e.g., fungi.

A bacterial treatment in accord with the invention may also be used to inhibit staining by staining fungi on logs and on structural wood cut therefrom.

DETAILED DESCRIPTION

According to the present invention there is provided a method for reducing the resin component of pulpwood and incompletely refined pulps. The method comprises the steps of applying to the pulpwood or pulp substrate a bacterial inoculum of at least one of the species selected from the group comprising *Pseudomonas fluorescens* and *Xanthomonas campestris*, and maintaining the substrate under conditions which allow bacterial growth for a time sufficient to effect a reduction in the resin component of the substrate by the bacteria.

In a preferred aspect, the inoculum of the invention may be applied to unrefined pulpwoods, such as cut timber in either debarked or undebarked form, by inoculating the timber, more particularly exposed wood surfaces such as produced by at least partial scoring in the case of undebarked timber, and maintaining the timber for a time sufficient to allow the bacteria to grow on and into the wood substrate and effect a reduction in the resin component thereof. In another preferred aspect, the inoculum is applied to refined pulpwood, particularly wood chips.

The inoculum may be in solid or liquid form. Whole liquid cultures or portions thereof may be used. The product may be lyophilized (freeze-dried) to obtain a dry inoculum or concentrated to be diluted with water for application, which forms are generally stored at temperatures that preserve desired viability. Liquid forms are usually stored frozen, typically at temperatures of from −5° C. to −80° C., more usually −10° C. to −75° C. Dry forms are similarly stored although some forms are often more stable and may be stored at higher temperatures than counterpart liquid forms. Inoculum compositions may comprise other ingredients such as preservatives and stabilizing agents or inert carriers introduced in certain types of drying processes.

Generally inocula may be applied to a wood substrate in various ways. Typically, the inoculum is applied in a systematic or methodical manner. For example, the inoculum can be distributed at intervals in an accumulated mass of refined pulpwood, or on the outer surface of a cut timber, preferably at regular intervals. More specifically, the inoculum can be distributed in a homogeneous or uniform manner, i.e. substantially throughout the mass of refined pulpwood. However, it is not necessary that each individual wood chip, sawdust particle and the like be inoculated. As little as 10% or even less, but typically from 20% to 50% of the individual pieces can be inoculated since the uninoculated pieces are accumulated in contact with the inoculated pieces. Upon growth, colonization will spread very easily.

A thorough or uniform inoculation of a mass of wood chips is generally reflected by the fact that the inoculated organism(s) grows substantially throughout the mass. Natural moisture in wood chips can facilitate growth and can be further supplied by water in preferred aqueous inocula. However, it may happen that some part of the mass, particularly the outer layer of a pile of refined wood pulp, will show little growth compared to the rest of the mass, or no growth at all, although it has been inoculated.

In practice, the inoculum may be sprayed onto wood chips or sawdust as they are discharged from the refining operation but before being accumulated into piles. For example, a wood chipping apparatus is generally provided with conveyor means which receive the newly prepared chips and convey them to the accumulating pile. A spray applicator containing the inoculum preparation may be conveniently adapted to the conveyor, preferably at the junction in the chipper where the chips become airborne e.g. free falling or tumbling, or at the very end of the conveyor so that chips are sprayed just before falling from the conveyor.

Alternatively, the inoculum may be applied to the wood chip pile in the course of its accumulation by more or less continuous spraying over the accumulating pile.

When treating pulps or refined pulpwood, the dosage of inoculum applied may vary depending upon several factors such as the wood being treated, condition or age of the wood, growth conditions, desired treatment time and the like, but will be sufficient upon growth to reduce pitch. In general, satisfactory results may be obtained upon application of an inoculum at a dosage or rate of $10^6$ to $10^{15}$ cells of bacteria, preferably $10^8$ to $10^{14}$ cells of bacteria, per 500 grams of pulp or refined pulpwood (such weight being normal, heat undried weight in a mass which does not drip water after standing for at least 20 minutes).

Chips which have been previously inoculated and incubated may be dispersed into fresh chips to effect or enhance inoculation. Such an inoculum is likely to be not biologically pure. However, it reflects the previous inoculation to the extent that the inoculum comprises the desired bacteria.

After inoculation, the accumulated substrate mass is maintained under conditions which will allow or promote the growth of the organism substantially throughout the mass. Given the fact that this will, in most cases, likely occur in open air and the mass therefore subjected to a wide variety of weather conditions, the maintenance of any given set of ideal conditions throughout the entire treatment period is usually too difficult to achieve and is often unnecessary in practice. It is generally sufficient that the mass be substantially maintained at a temperature at which the inoculating organism grows while avoiding higher temperatures at which it dies. For example, temperatures between 10°–40° C. are more suitably used.

In mild or warm weather conditions, it is not necessary to influence the environmental temperature and the inoculated mass may be left to stand in open air without special maintenance. In cold weather conditions, it may be desirable to provide the inoculated mass with means for maintaining the more suitable temperatures. This may be a heat-retaining covering placed over or on the inoculated mass such as a large plastic sheet. Alternatively, the ground base on which is placed the inoculated mass may be provided with heating pipes or a plurality of openings for releasing warm air or steam. In a similar manner, a concrete "igloo" or similar structure which can be internally heated and emit radiant heat may be used to support the accumulated mass of pulpwood. When providing heating means, it would also be desirable to control the moisture conditions to avoid an excessive dryness. In view of this, means for venting the heat or steam would need to be adequate. However, due to the heat generated in an accumulated mass from, e.g., bacteria growth, and other microbial or natural effects, operation under many cold weather conditions may proceed satisfactorily with little or no assistance.

The period of time during which the inoculated refined pulpwood mass is treated may vary considerably depending upon a number of factors including the desired extent of resin removal, the temperature and moisture conditions, the extent of inoculation and the like. However, satisfactory results have been generally obtained with bacterial inocula after a period of time extending from 3 to 40 days i.e., pitch reduction under preferred conditions of about 20% or more, the preferred treatment time being 4 to 20 days after the inoculation.

Treatment of unrefined pulpwood, such as cut timbers, may be carried out for a longer time than that of refined pulpwood and may extend up to 3 months. However, treatment of unrefined pulpwoods with the indicated bacteria generally should be conducted for periods which effect desired pitch reduction. Incula concentrations for unrefined pulpwood may be similar to those for refined pulpwood and applied over from 10% to 100% of available surfaces, more usually over 15% to 60% of the available surfaces. When a log is undebarked, it is desirably scored lengthwise and exposed wood areas inoculated as hereinafter described.

The treatment of wood with bacteria in accord with the invention suppresses or reduces the growth of staining fungi on unsterilized wood and is indicated to provide the added benefit of reducing bleach requirements in the making of paper and the like. The penetration of the bacteria and removal of pitch is also indicated to benefit the pulping process. The effect of suppressing staining fungi also make the bacteria useful in treating wood raw material used to make structural wood such as lumber and the like, including that used to make furniture, and also in the treatment of structural wood itself. The natural staining of wood used for structural woods is a problem in the lumber and related industries, particularly when woods are to be finished by painting or staining. Hence, the present invention also provides a process of reducing color staining by staining fungi on structural wood cut from a log comprising applying to exposed wood surface areas of a debarked or bark-retaining timber log or of structural wood itself an iunoculum of *Pseudomonas fluorescens* or *Xanthomonas campestis*, and allowing the inoculated bacteria to grow on and into the inoculated log or structural wood.

When the substrate is bark-retaining, the exposed surface areas are typically the log ends and damaged bark areas along the log length. Desirably, bark-retaining logs will also be scored along their length and scored areas also inoculated, as in practice of the invention to remove pitch for making paper and the like.

Scoring of the bark near their cut ends in the process of lengthwise scoring will assist in reducing staining infestation at the log ends, and may enable inoculation of the ends to be dispensed with, but desirably the exposed log ends are always inoculated. The intervals between scorings may vary considerably depending largely on factors which affect growth such as the level of inoculation and ambient conditions. In general, intervals between scorings can range from 6 to 36 inches, and preferably range between 8 to 20 inches both lengthwise and around the log circumference, and the bacteria inoculated into the scorings which generally will be carried out to a depth sufficient to substantially reach or expose the under-the-bark wood. If and when logs are to be debarked, and then stored, it is within the scope of the invention to inoculate at least 50% of exposed and debarked surface area with the bacteria to protect against staining fungi, preferably at least 80%. Whether or not the logs are debarked, it is desirable to treat the log in no more than two weeks after harvest (cutting down of the tree), preferably in no more than one week and more preferably in no more than 4 days. Moreover, a considerable expense is encountered in the structural wood industry in protecting structural wood after cutting from logs against the color staining fungi which could infect the wood before or after cutting to form the structural wood, typically by spraying with an environmentally unsound fungicide such as pentachlorophenol. It is further within the scope of this invention to protect such structural wood against staining fungi by inoculating at least the lengthwise surfaces, or at least 50% of the surface area, preferably at least 80% and more preferably all surfaces, of such structural wood with the pitch degrading bacteria. The bacteria is then allowed to grow on the structural wood which is maintained under environmental conditions sufficient to permit growth for at least about 14 days. Such inoculation desirably takes place no more than two weeks after the structural wood is cut from its log source, preferably in no more than one week, more preferably in no more than 4 days and most preferably in no more than 2 days. Such treatments are particularly useful to inhibit staining when the structural wood is stored and/or shipped for long periods in environments where staining fungi may be present, such as in ships or trucks which had previously carried infected wood forms such as logs, wood chips and the like.

In carrying out the invention, whether to inhibit staining and/or reduce pitch, it is generally preferred to use an aqueous inoculum containing bacterial cells in a concentration generally in the range of from $10^6$ to $10^{15}$ cells/ml., preferably $10^8$ to $10^{14}$ cells/ml., more usually $10^9$ to $10^{13}$ cells/ml. For surface treatments of unrefined pulpwood, structural wood and the like, such an inoculum will be used to wet the surface area(s) to be inoculated, and may be applied up to the point of run off. Adjuvants may be included in such inocula such as anti-transperants (to inhibit desiccation) and stickers to insure maintenance of the cell at the inoculated surface until growth is established. Carboxymethylcellulose is an example of such an adjuvant. An inoculum preferably has a pH of from pH 5.5 to 10, more preferably pH 6 to 9, and may be bufferred in this range to assist bacterial growth while discouraging undesired growth such as staining fungi. Desirably, the inoculum is biologically pure, but for the bacterium to be inoculated, and such bacterium obtained from a biologically pure culture. Healthy, vigorously growing bacteria are desirable for use in the inoculum.

The bacteria employed in this invention are indicated to infect a wide variety of wood types or genera processed by industry for structural woods, paper products and the like. These include both Gynmosperms and Angiosperms, and in particular both hardwoods and softwoods. Particular classes or types of wood therefore include without limitation conifers such as firs, spruce, pines and cedars and hardwoods such as oak, maple, aspen, hickory, beech, eucalyptus and birch. Gymmosperms or softwoods such as pines generally have high pitch content and are readily colonized by the pitch degrading bacteria. Hardwoods, particularly those with low pitch contents, may in some instances require more thorough or high dose inoculation of the pitch degrading bacteria. In order to ensure optimum germination and/or bacterial growth, and bacterial nutrients may be also applied to the log or wood in such cases, although the use of nutrients is generally unnecessary and less preferred.

CLASSIFICATION AND CHARACTERISTICS OF BACTERIA

The above referred to bacterial species *Pseudomonas fluorescens* is herein indicated to include and be represented by the isolates which are hereinafter also referred to as "B-5" and "B-24". The above referred to bacterial species *Xanthomonas campestris* is herein represented by the isolate hereinafter also referred to as "B-29".

The above indicated bacteria B-5, B-24 and B-29 were subjected to various investigations and evaluations in order to determine their identification and characteristics. The nature and results of these investigations and evaluations, and comment thereon, is given below paragraph A), B) and C), below, and include the specification information given in Tables A and B, below:

A) Source, Staining and Enzyme Response.

a-1) Procedures: Biological pure cultures of the bacterial isolates were each separately subjected to Gram's staining technique to determine Gram-positive or Gram-negative cell wall characteristics. Clark G. L. Eds. 1973, *Staining Procedures Used by the Biological Stain Commission* (3d ed., Baltimore Williams and Wilkins. pp. 247–251). Lenette E. H., Balows A., Hausler W. J. Jr., and Shadomy H. J. (ed.). 1985. *Manual of Clinical Microbiology*, (4$^{th}$ Ed. American Society for Microbiology, Washington, D.C. pp. 1095). Bacteria retaining crystal violet after decolorization were denoted Gram-positive and those that did not were Gram-negative. The Kovacs Oxidase test was also used to further categorize these isolates. Cytochrome oxidase is a heme-containing protein component in the respiratory chain of enzymes and is found in bacteria that can use oxygen. Facultative and strict anaerobes do not have the Cytochrome oxidase protein and test negative, see Kovacs, N. 1956 "Identification of *Pseudomonas pyocyanea* by the Oxidase Reaction", Nature (London) 178:703. The test for lipase activity was conducted using Sierra Medium in accord with the procedure described by Atlas, M. R., 1993, Handbook of Microbiological Media, 807, L. C. Parks ed. CRC Press, Florida, U.S.A. and Sierra, G., 1957, *A Simple Method for the Detection of Lipolytic Activity of Micro-organisms and Some Observations on the Influence of the Contact Between Cells and Fatty Substrates*, Antoine Van Leeuwenhock 23, 15–22, see also Merieau, A. et al., *Temperature Regulation of Lipase Secretion by Pseudomonas fluorescens Strain MFO*, Applied Microbiology and Biotechnology, 39:104–109 (1993).

a-2) Results of the investigations indicated in a-1), above, and source information are given below in Table A.

TABLE A

| Bacteria Culture | Isolate Source | Gram Staining | Shape | Oxidase | Lipase |
|---|---|---|---|---|---|
| B-5 | loblolly pine Southern Virginia, U.S.A. | negative | rods | positive | positive |

TABLE A-continued

| Bacteria Culture | Isolate Source | Gram Staining | Shape | Oxidase | Lipase |
|---|---|---|---|---|---|
| B-24 | Rothschild, Wisconsin, USA aspen | negative | rods | positive | positive |
| B-29 | Southern Virginia, USA loblolly pine | negative | rods | negative | positive |

B) Morphological Characteristics b-1) Colony morphology and growth characteristics were also determined in culture, including form, elevation, color and margin of the bacterial colonies, by observing colonies growing on plates of nutrient media using a stereoscope according to recognized standard procedures. For each bacteria a wet mount was also prepared and placed under a bright-field microscope and cellular morphologic characteristics were observed including size, shape and motility of the bacterial cells, also according to recognized standard procedures.

b-2) The results of the investigations and evaluations indicated in b-1), above, are given below in Table B.

TABLE B

| | Colony Morphology | | | | |
|---|---|---|---|---|---|
| Bacteria | Entire Col. | Elevation | Surface | Motility | Size |
| B-5 | Entire | Convex | Smooth | Yes | Approx. 0.82–1.64 µm |
| B-24 | Entire | Convex | Smooth/ Glistening | Yes | 0.82–1.64 µm |
| B-29 | lobate | Convex | Smooth/ rough | Yes | 0.82–1.64 µm |

C) American Type Culture Collection (ATCC), Rockville, Md. USA c-1) The isolates were submitted to the ATCC for confirmation/identification of species using its Rapid Identification procedure SC 3299 and the well known Biolog System (Biolog, Inc., 3447 Investment Boulevard, Suite 3, Hayward, Calif. 94545 USA) in effect with ATCC as of April, 1994. Information and equipment for the Biolog analysis is readily available from Biolog, Inc. and analysis according to the Biolog System is available as a service from organizations such as the ATCC.

c-2) In addition to confirming characterizing information given above in paragraphs A) and B), the ATCC gave glucose (open and closed) results as follows:

B-5) Glucose open (positive), Glucose closed (negative);

B-24) Glucose open (positive), Glucose closed (negative); and

B-29) Glucose open (negative), Glucose closed (negative).

The ATCC identified B-29 as the species *Xanthomonas campestria* (Biolog Microplate similarly to this species 0.701); B5 as the species *Pseudomonas fluorescens* (Biolog Microplate similarly to this species 0.879); and also indicated its best identification of B-24 as also *Pseudomonas fluorescens* with many strain characteristics distinct from B-5 by the Biolog analysis including minor points of similarly with *P. fuscovaginae* and *P. aurantiaca* that are not shown by B-5 (Biolog species similarly *P. fluorescens* (0.341), *P. fuscovaginae* (0.174) and *P. aurantiaca* (0.038)).

Hence, for purposes of definition herein, a bacteria is assigned to a species when its morphological characteristics as reported Table B, its staining and shape are consistent with the species and it has a greater similarly with the species than any other species in the applicable 96-well Biolog Microplate analysis. Because of the apparent unusual species characteristic of B-24 in the Biolog, indicating a valuable and heretofore unknown strain, the results of the 96-well Biolog GN Microplate analysis are given for each well compartment with whole number results first in parenthesis and the response indication given second in parenthesis, as follows:

A1(0)(–); A2(21)(–); A3(13)(–); A4(17)(–); A5(276)(+); A6(240)(+); A7(–7)(–); A8(162)(+); A9(13)(–); A10(17)) (–); A11(186)(+); A12(1)(–); B1(–1)(–); B2(625)(+); B3(3) (–); B4(51)(V); B5(16)(–); B6(917)(+); B7(499)(+); B8(3) (–); B9(5)(–); B10(33)(V); B11(815)(+); B12(377)(+); C1(11)(–); C2(9)(–); C3(45)(V); C4(3)(–); (C5(–4)(–); C6(16)(–); C7(–3)(–); C8(729)(+); C9(11)(–); C10(3)(–); C11(369)(+); C12(276)(+); D1(402)(+); D2(1185)(+); D3(1211)(+); (D4(135)(+); D5(81)(V); D6(457)(+); D7(786)(+); D8(57)(V); D9(342)(+); D10(13)(–); D11 (1013)(+); D12(998)(+); E1(951)(+); E2(69)(+); E3(7)(–); E4(1074)(+); E5(94)(+); E6(965)(+); E7(519)(+); E8(623) (+); E9(791)(+); E10(364)(+); E11(256)(+); E12(893)(+); F1(42)(+); F2(426)(+); F3(169)(+); F4(36)(V); F5(355)(+); F6(364)(+); F7(311)(+); F8(907)(+); F9(752)(+); F10(981) (+); F11(14)(–); F12(98)(+); G1(981)(+); G2(348)(+1); G3(542)(+); G4(248)(+); G5(21)(–); G6(591)(+); G7(597) (+); G8(56)(V); G9(395)(+); G10(68)(V); G11(614)(+); G12(683)(+); H1(893)(+); H2(583)(+); H3(71)(V); H4(–4) (–); H5(203)(+); H6(668)(+); H7(474)(+); H8(49)(V); H9(610)(+); H10(160)(+); H11(56)(V); H12(258)(+); wherein "V" is borderline.

It is apparent from the foregoing and the results in the following examples that the many characteristic differences between B-5 and B-24 do not materially affect the ability of these organisms to effectively degrade pitch, indicating that such desired ability is possessed by bacterium which can mainly or wholly have the character of the assigned species, ie. *Pseudomonas fluorescens* in the case of B-5 and B-24 and *Xanthomonas campestris* in the case of B-29. An important performance characteristic associated with the indicated species in degrading pitch is indicated to be the ability to penetrate wood substrate by growing below the surface and well into the wood. Such penetration bacteria have an ability to colonize the ray parendryma cells and resin canals where the pitch resides and also desirably have ability to degrade pit membranes and move from cell to cell as can be determined, e.g. by pitch reduction analysis and by microscopic examination, as described by Blanchette, et al., Biological Degradation of Wood, Advances In Chemistry Series 225, 1990 Archaeological Wood: Properties, chemistry and Preservation, R. M. Rowell and R. J. Barbour Editors. Such penetrating, pit-degrading bacteria are distinct from those classified as tunnelling, erosion and cavitation bacteria which degrade lignin and cellulose. Another important performance characteristic of the bacteria of our invention is the ability to selectively reduce the pitch content of wood without subtantially the degrading the cellulose, hemicellulose or lignin content of the wood. Hence, the indicated bacteria are able to colonize wood and grow well within the wood while degrading pitch, yet they can be clarified as non-wood degrading bacteria which leave the normally sought-for or sound wood components of cellulose, hemicellulose and lignin essentially unaffected. The *Pseudomonas fluorescens* and *Xanthomonas campestris* species are indicated to generally possess these various important performance characteristics. A pitch degrading bacteria is also indicated to possess lipase activity as determined by the above indicated Sierra Medium assay.

The indicated isolates B-5, B-24 and B-29 which have been deposited with the NRRL represent particularly desirable and potent bacteria for degrading pitch in wood. Variants and mutations of these isolates which substantially retain at least the pitch degrading properties of the isolates (as determined after 14 days of growth at room temperature after inoculation at a dose of $10^{14}$ cells per 500 grams on wood chips of the wood type from which the isolates were naturally obtained, the wood chips being obtained from freshly harvested, e.g. one day old timber) will also be valuable means for reducing pitch. Such variants and mutants of these isolates and their progeny may be obtained in a variety of ways as is well known such as in the growth, use, mating and treatment of the bacterial cells (and those of their progeny).

DEPOSITS

We have under the Budapest Treaty deposited with the Northern Regional Research Center (NRRL) at Peoria, Ill., U.S.A. the following bacteria referred to herein, which deposits were assigned the Accession Numbers given below along with their date of deposit.

| Bacteria | Accession No. | Deposit Date |
| --- | --- | --- |
| (1) *Pseudomonas fluorescens* (B-5) | NRRL B21432 | April 11, 1995 |
| (2) *Xanthomonas campestris* (B-29) | NRRL B21430 | April 11, 1995 |
| (3) *Pseudomonas fluorescens* (B-24) | NRRL B21431 | April 11, 1995 |

EXPERIMENTAL

General Procedures: Cultures and Inoculation

Various evaluations are made on pulpwood substrates to determine pitch reduction and growth. For evaluation of softwood characteristics, sterile and non-sterile Southern Yellow Pine wood chips were used. For evaluation of hardwood characteristics, non-sterile aspen wood chips were used, as well as birch and a mixed hardwood containing 75% oak. Wood chips are stored at 5° C. prior to evaluation. Each evaluation was performed on substrates of the same wood species and upon wood chips samples which were obtained from the same wood chip source. For each test, individual sample lots of wood chips were first weighed, after which the wood chip samples to be sterilized were heated in an autoclave at 121° C. for about 90 minutes and allowed to cool to room temperature prior to the initiation of a test. The wood chip samples which were to be in non-sterile form were untreated and used in their natural condition. Individual sample lots were prepared by placing measured amounts of wood chips into individual transparent plastic bags; the bags were of sufficient size such that they were closeable (although not hermetically sealable). The use of a transparent bag allowed for the visual inspection of the growth of chips, and to further allow for admission of ambient light to the sample of wood chips being evaluated.

Pitch Content Evaluations:

The pitch content of substrates is determined in accord with the standard TAPPI procedure T204 OM-88 and may be expressed as mg. of pitch content per gram of substrate which had been extracted with dicloramethane (DCM) or with toluene/ethanol. The weight of the residue is determined in mg. as the pitch content and expressed either as mg. of pitch content per gram of substrate or as a percentage of pitch in original the substrate (% extractives). Pitch reduction is generally indicated when the inoculated fungus show a statistically significant reduction in pitch content compared with the control. Preferably, the pitch is reduced at least 10%, and more preferably at least 15% compared to the control. Pitch evaluations may be conducted on both sterile and non-sterile substrates. Evaluations on sterilized substrates will usually eliminate any possible influence of other organisms which naturally infect the substrate. An evaluation on a sterilized substrate can be generally considered the more objective measure of the fungus to reduce pitch on a particular substrate. However, whether conducted on a sterilized or non-sterilized substrate, pitch reduction is generally evaluated relative to an untreated control which is sterilized (for sterilized substrate tests) or held in the frozen state during the test period (for non-sterilized substrate evaluation). In general, it is desired to achieve a pitch reduction relative to such a control of at least 20% in no more than 21 days after inoculation, preferably in no more than 14 days. Particularly good results are indicated when pitch is reduced 25% in no more than 21 days, and especially when such reduction is achieved in no more than 14 days.

Nutrient

References in the following examples to a nutrient are to the commercially available nutrient known as BACTO NUTRIENT BROTH sold by DIFCO LABORATORIES, Detroit, Mich. as a water soluble powder containing, proportionately, 3 g. of beef extract and 5 g. peptone (low molecular weight proteins from hydrolyzed animal tissues, see Atlas, M. R. 1993, Handbook of Microbiological Media., Edited by L. C. Parks, CRC Press, Florida, page 2). One liter of the water diluted BACTO NUTRIENT BROTH containing the above indicated amounts (total of 8 g.) has a pH of about pH 6.8.

EXAMPLE 1

The bacterial isolates B-5 and B-29 were selected from preliminary screening for testing to determine if they could reduce the amount of dichloromethane extractive over time.

Bacteria were transferred from plates of nutrient agar using a sterile inoculation loop to nutrient broth (8 gm/L of Difco-Bacto Nutrient) in 125 ml flasks and incubated in shake culture for growth at room temperature for 20 hours. Inocula were prepared by placing one ml of cells from each shake culture in a 125 ml flask with 99 ml of the nutrient broth to bring the total volume to 100 mL, and incubating the resulting cultures for 24 hours. At this point the resulting cultures/inocula had the following concentrations of bacteria cells:

| Culture | Cells per ml |
|---------|--------------|
| B-5 | $3.39 \times 10^9$ |
| B-29 | $1.96 \times 10^9$ |

Bacterial cells were enumerated using the well known viable-cell count method which involves a series of dilutions with the cultures to obtain dilution factors such as $1 \times 10^5$, $1 \times 10^6$ and $1 \times 10^7$ cells per ml. For each dilution one ml is removed and placed in a Petri dish and cool nutrient agar is added. After 24 hours individual colonies of bacteria are counted and multiplied by the dilution factor. This method gives the number of viable cells present per ml of the cell-containing mass being evaluated, such as a diluted or concentrated cell culture or an inoculum.

Two plastic bags, each containing 500 grams of fresh nonsterile southern loblolly pine chips, were separately inoculated with 100 ml of each inoculum prepared as described above. The bacterial inoculum was poured into the bags with the nonsterile wood chips and agitated to distribute bacterial cells evenly. These bags of inoculated chips were left to incubate at room temperature for 14 days (one control treatment consisted of 100 ml of nutrient broth while another control received only water).

After 14 days inoculated and control chips were removed, air-dried for one day and subjected to dichloromethane extractive analysis. Also for each treatment, three treated chips were removed from each bag and five 2 cm×2 cm wood subsamples were taken from each chip and placed on nutrient agar plates for 24 hours. Bacteria growing in these plates were streaked onto nutrient agar to obtain pure cultures. The non-sterile control treated sample received only nutrient broth and contained three different wild type bacteria species. Results of the extractive analysis are reported in Table 1.

TABLE 1

Percent dichloromethane (DCM) extractives in bacterial treated and nontreated loblolloy pine chips with nutrient broth

| Treatment | Time Days | DCM % | % DCM Loss |
|-----------|-----------|-------|------------|
| Frozen control | 0 | 3.53 | — |
| Aged controls (non-sterile without Nutrient broth) | 14 | 3.13 | 11.3 |
| Non-sterile Control with Nutrient broth | 14 | 2.27 | 35.5 |
| B-5 | 14 | 2.10 | 40.5 |
| B-29 | 14 | 1.71 | 51.5 |

As shown by Table 1, the bacteria B-5 and B-29 positively reduced pitch on non-sterile wood chips. It was also noted that the wood chips treated with B-5 and B-29 were brighter than the non-sterile control chips treated only with nutrient broth and also brighter than the Aged Control (non-sterile chips without nutrient broth).

EXAMPLE 2

The purpose of this study was to determine if bacterial isolates Pseudomonas fluorescens (B-5) and (B-24) could reduce the amount of extractives in nonsterile aspen chips in substantial absence of nutrient.

Bacteria were grown in flasks of nutrient broth for 56 hours on an orbital shaker. After this time each isolate was centrifuged to collect the bacterial cells and to remove spent nutrient broth. Inocula were prepared by placing concentrated cells from each isolate in a graduated cylinder and bringing the total volume to 100 ml. with water. These inocula contained $1.4 \times 10^{10}$ cells/ml of B-5 and $2.3 \times 10^{10}$ cells/ml of B-24 and each inoculum (100 ml.) was poured into a bag with 500 grams of nonsterile aspen chips. The bags with chips were then shaken to distribute inoculum evenly. One-hundred ml of water was added with no bacterial cells for a control. After two weeks several aspen chips from each bag were removed and bacterial isolations made on nutrient agar. Bacteria with similar cultural characteristics as Pseudomonas fluorescens B-5 and B-24 were recovered from each bag of chips into which they were inoculated. Chips were air dried and the amount of solvent-soluble, non-volatile material (resin) was determined by ethanol-toluene extractive analysis. Also, fresh frozen aspen chips were used to determine the original amount of resin at time zero. All evaluations were made in duplicate and the results averaged. These results are given below in Table 2.

TABLE 2

| Treatment | Time Days | Ethanol/Toluene % Extractions Mean | Standard Deviation | % Extractives Removed |
|---|---|---|---|---|
| Frozen control | 0 | 3.27 | 0.17 | — |
| Control with water | 14 | 2.65 | 0.07 | 18.9 |
| Pseudomonas fluorescens B-5 | 14 | 2.22 | 0.03 | 32.1 |
| Pseudomonas fluorescens B-24 | 14 | 2.25 | 0.00 | 31.1 |

EXAMPLE 3

Isolates of the bacteria B-5 and B-29 were each transferred from nutrient agar plates to a flask and grown in 100 ml. of nutrient broth (8 g Difco Nutrient Broth/liter) on an orbital shaker. After 48 hours 100 ml of each culture containing $1.30 \times 10^9$ cells/ml of B-5 and $8.75 \times 10^9$ cells/ml of B-29 was poured into separate bags each containing 500 g of loblolly pine chips which had been sterilized by autoclaving at about 140° C. for 90 minutes. The experiment for each culture was done in triplicate. The bags with chips were then shaken to distribute inoculum evenly. Control chips which had been sterilized were treated with 100 ml of nutrient broth with no bacterial cells.

After 2 weeks several chips from each bag were removed and isolations made on nutrient agar or in liquid culture. Isolates B-5 and B-29 were recovered from each bag of chips that they were inoculated in and no bacteria were isolated from the controls. Chips were air-dried and two dichloromethane extractive analyses were done. Two dichloromethane extractive analysis were done for each sample and an average was taken to determine percent extractives removed. The results are reported below in Table 3.

TABLE 3

Present dichloromethane extractives (DCM) in bacterial treated and nontreated sterile loblolly pine chips over 2 weeks.

| Treatment | Total Cells Added | Total Time Days | DCM % | % Extractives DCM Loss |
|---|---|---|---|---|
| Frozen control | 0 | 0 | 4.62 | — |
| Control with nutrient broth | 0 | 14 | 3.60 | 22.0* |
| Pseudomonas fluorescens B-5 | $1.30 \times 10^{11}$ | 14 | 3.07 | 33.6 |
| Xanthomonas campestris B-29 | $8.75 \times 10^{11}$ | 14 | 3.50 | 24.2 |

*loss due to autoclaving

EXAMPLE 4

The purpose of this study was to determine if bacteria isolates B-5 Pseudomonas fluorescens and B-29 Xanthomonas campestris could reduce the amount of extractives in nonsterile loblolly pine chips after a two week period by adding bacterial cells in water without added nutrients.

Bacteria were transferred from nutrient agar plates to a flask with nutrient broth for each isolate and placed on an orbital shaker. After 24 hours for each bacterial isolate, 6 ml of each culture containing $1.89 \times 10^9$ cells/ml of B-5 and $6.85 \times 10^9$ cells/ml of B-29 were transferred to a flask with 600 ml of nutrient broth and placed on an orbital shaker. After 24 hours each isolate was centrifuged to collect the bacterial cells and to remove spent nutrient broth. Inocula were prepared by placing concentrated cells in a cylinder and bringing the total volume to 100 ml. with tap water. The inocula concentrations were $2.63 \times 10^9$ cells/ml of B-5 and $9.05 \times 10^9$ cells/ml of B-29. The 100 ml of inoculum from each isolate were poured into a bag containing 500 g of nonsterile loblolly pine chips. The bags with chips were then shaken to distribute inoculum evenly. For each treatment (including control) 2 bags of 500 grams each were inoculated. 100 ml of tap water with no bacterial cells was added to 500 g. of chips for a control.

After 2 weeks several chips from each bag were removed and isolation made on nutrient agar or broth. Isolates B-5 and B-29 were recovered from each bag of chips wherein they were inoculated. Chips were then air dried. Two dichloromethane extractive analyses were done for each sample and an average was taken to determine percent extractives removed. Results are below in Table 4.

TABLE 4

| Treatment | Total Cells Added | Time Days | DCM % | % Extractives DCM Loss |
|---|---|---|---|---|
| Frozen control | 0 | 0 | 3.83 | — |
| Control with water | 0 | 14 | 3.32 | 13.3 |
| Pseudomonas fluorescens B-5 | $2.63 \times 10^{11}$ | 14 | 2.95 | 22.9 |
| Xanthomonas campestris B-29 | $9.05 \times 10^{10}$ | 14 | 3.15 | 21.6 |

EXAMPLE 5

The purpose of this study was to determine if bacterial isolate B-24 (a Pseudomonas fluorescens) could reduce the amount of extractives in fresh mixed hardwood chips after a two week period. The bacterial isolate was transferred from a nutrient agar plate to a flask with nutrient broth (8 g Difco Nutrient Broth/Liter) and placed on an orbital shaker. After 48 hours the isolate was centrifuged to collect cells and remove spent nutrient broth. Recovered cells were combined with fresh nutrient broth (8 g Difco Nutrient Broth/Liter) to bring the total volume to 100 ml which contained $9.2 \times 10^9$ cells/ml of B-24. This 100 ml as an inoculum was poured into a bag containing 500 g of nonsterile mixed hardwoods (75% oak and the balance mainly maple, ash and hickory). 100 ml fresh sterile nutrient broth added to 500 g. chips was used with no cells as a control. Both the control and inoculated trials were run in duplicate. The bags of chips were then shaken to distribute contents evenly.

After two weeks several chips from each bag were removed and isolates made on nutrient agar or liquid culture. Bacterial isolate B-24 was recovered from each bag of chips wherein it was inoculated. Chips were air dried and the toluene and ethanol extractive analyses were respectively done for each sample and an average was taken to determine percent extractives removed. Results are reported in Table 5, below.

TABLE 5

Percent toluene/ethanol extractives from nonsterile bacterial treated mixed hardwoods after a two week period

| Treatment | Total Cells Added | Time Days | Toluene Ethanol % | Percent Extractives Removed |
|---|---|---|---|---|
| Frozen control | 0 | 0 | 4.25 | — |
| Control with nutrient broth | 0 | 14 | 2.70 | 36.4 |
| B-24 Pseudomonas fluorescens | $9.2 \times 10^{11}$ | 14 | 2.55 | 40.0 |

EXAMPLE 6

The purpose of this study was to determine if bacterial isolates B-5 *Pseudomonas fluorescens* and B-29 *Xanthomonas campestris* could reduce the amount of extractives in nonsterile loblolly pine chips after a two week period by adding bacterial cells in water.

Bacteria were transferred from nutrient agar plates to a flask with nutrient broth for each isolate and placed on an orbital shaker. After 56 hours each isolate was centrifuged to collect the bacterial cells and to remove spent nutrient broth. Inocula were prepared by placing concentrated cells from each isolate in a cylinder and bringing the total volume to 100 ml. with tap water. These inocula contained $1.61 \times 10^{10}$ cells/ml of B-5, and $1.41 \times 10^{10}$ cells/ml of B-29 and each resulting inoculum (100 ml.) was poured into a bag with 500 grams of nonsterile loblolly pine chips. The bags with chips were then shaken to distribute inoculum evenly. 100 ml of tap water was added with no bacterial cells for a control.

After 2 weeks several chips from each bag were removed and isolation made on nutrient agar. Bacteria with similar cultural characteristics as B-5 *Pseudomonas fluorescens* and B-29 *Xanthomonas campestris* were recovered from each bag of chips. Chips were air dried and the amount of solvent-soluble, non-volatile material (resin) was determined by dichloromethane extractive analysis. Also, two bags each of 500 g fresh frozen chips were used to determine the original amount of resin at time zero. Dichloromethane extractive analysis was done for each 500 g bag of chips and the average of two trials from each treatment was taken to determine percent extractives removed. The results are in Table 6 below.

TABLE 6

Percent dichloromethane extractives (DCM) in nonsterile bacterial treated and nontreated loblolly pine chips

| Treatment | Time Days | DCM Extractives % Mean | % Standard Deviation | DCM % Extractives Removed |
|---|---|---|---|---|
| Frozen control | 0 | 5.60 | 0.53 | — |
| Control with water | 14 | 4.50 | 0.84 | 19.6 |
| P. fluorescens B-5 | 14 | 3.10 | 0.35 | 44.6 |
| X. campestris B-29 | 14 | 3.60 | 0.17 | 35.71 |

EXAMPLE 7

The purpose of this study was to determine if bacterial isolates B-5 *Pseudomonas fluorescens* and B-29 *Xanthomonas campestris* could reduce the amount of extractives in nonsterile maple chips after a two week period by adding bacterial cells in distilled water.

Bacteria were grown in flasks of nutrient broth for 56 hours on an orbital shaker. After this time each isolate was centrifuged to collect the bacterial cells and to remove spent nutrient broth. Inocula were prepared by placing concentrated cells from each isolate in a cylinder and bringing the total volume to 50 ml. with tap water. These inocula contained $2.3 \times 10^{12}$ cells/ml. of B-5 and $4.75 \times 10^{12}$ cells/ml. of B-29 and were each separately poured into a bag with 500 g of nonsterile maple chips. The bags with chips were then shaken to distribute inoculum evenly. 50 ml distilled water was added with no bacterial cells, as a control.

Chips were air dried and the amount of solvent-soluble, non-volatile material (resin) was determined by ethanol-toluene extractive analysis, two bags each of 500 g fresh frozen chips being used to determine the original amount of resin at time zero. One ethanol-toluene extractive analysis were done for each 500 g bag of chips and the average of two from each treatment was taken to determine percent extractives removed. The results are in Table 7, below.

TABLE 7

Percent ethanol-toluene extractives (ET) in nonsterile bacterial treated and nontreated maple chips

| Treatment | Time Days | ET % Mean | Standard Deviation | % Extractives Removed |
|---|---|---|---|---|
| Frozen control | 0 | 2.12 | 0.38 | — |
| Control with water | 14 | 2.10 | 0.21 | 1.2 |
| P. fluorescens B-5 | 14 | 1.82 | 0.03 | 14.1 |
| X. campestris B-29 | 14 | 1.57 | 0.03 | 25.8 |

EXAMPLE 8

The bacterial isolates *Pseudomonas fluorescens* (B-5), and *Xanthomonas campestris* (B-29) were used to reduce and pitch in nonsterile birch chips. Bacteria were grown in flasks of nutrient broth for 56 hours on an orbital shaker. After this time each isolate was centrifuged to collect the bacterial cells and to remove spent nutrient broth. Inocula were prepared by placing concentrated cells of each isolate in a graduated cylinder and bringing the total volume to 50 ml. with tap water. These inocula contained $2.3 \times 10^{12}$ cells/ml. of B-5 and $4.75 \times 10^{12}$ cells/ml. of B-29 and each resulting inoculum (50 ml.) poured into a bag with 500 grams of nonsterile birch chips. The bags with chips were then shaken to distribute inoculum evenly. Fifty mls of water was added with no cells for a control. After two weeks several birch chips from each bag were removed and isolations made on nutrient agar. Bacteria with similar cultural characteristics as *Pseudomonas fluorescens* (B-5) and *Xanthomonas campestris* (B-29) were recovered from each bag of chips in which they were inoculated. Chips were air dried and the amount of solvent-soluble, non-volatile material (resin) was determined by ethanol-toluene extractive analysis. Also, two bags each having 500 grams of fresh frozen birch chips were used to determine the original amount of resin at time zero. Results were the average of two replication of each treatment and are reported below in Table 8.

TABLE 8

| Treatment | Time Days | % Extractives Mean | Standard Deviation | % Extractives Removed |
|---|---|---|---|---|
| Frozen control | 0 | 2.80 | 0.07 | — |
| Control with water | 14 | 2.60 | 0.21 | 7.0 |
| Pseudomonas fluorescens B-5 | 14 | 2.25 | 0.07 | 19.6 |
| Xanthomonas campestris B-29 | 14 | 2.30 | 0.0 | 17.8 |

An analysis of loblolly pine wood chips treated as in Example 6, above, showed by gas chromatography analysis a reduction (loss) of between 40–80% of its content of 7 different resin acids (total resin acid loss 50.4%) and of between 19.2–61.3% of fatty acids (total fatty acid loss of 57.4%).

What is claimed is:

1. A process for reducing the pitch content of pulpwood or of pulp comprising applying to the pulpwood or pulp an inoculum of a bacterium of Pseudomonas fluorescens, the inoculum being in an amount sufficient upon bacterial growth from the inoculation to reduce the pitch content of the pulpwood or pulp, and maintaining the inoculated pulpwood or pulp under conditions which allow bacterial growth from the inoculation for a time sufficient to effect a reduction of the pitch content of the pulpwood or pulp by such inoculated bacterial growth.

2. The process of claim 1 in which unsterilized pulpwood is inoculated to reduce its pitch content.

3. The process of claim 2 in which the unsterilized pulpwood is unsterilized refined pulpwood, in which the inoculated refined pulpwood is accumulated in a mass and in which the accumulated mass is maintained under conditions which allow bacterial growth for a time sufficient to effect a reduction of the pitch content of the pulpwood by the inoculated bacterial growth.

4. The process of claim 3 in which the refined pulpwood is wood chips and the inoculum is applied by spraying of wood chips with the inoculum prior to accumulation of the wood chips in the mass.

5. The process of claim 1 in which the inoculum is obtained from a biologically pure bacterial culture.

6. The process of claim 4 in which the bacterium is a Pseudomonas fluorescens having the ability to reduce pitch on freshly harvested, unsterilized loblolly pine wood chips that is possessed by the bacterium of NRRL Accession No. B21432.

7. The process of claim 4 in which the bacterium is a Pseudomonas fluorescens having at least the ability to reduce pitch freshly harvested on unsterilized aspen wood chips that is possessed by the strain of NRRL Accession No. B21431.

8. The process of claim 1 in which first stage mechanical pulp is treated to reduce its pitch content.

9. The process of claim 2 in which a debarked or undebarked timber log is treated to reduce its pitch content.

10. The process of claim 1 in which the inoculated pulpwood or pulp is maintained under bacterial growth conditions for a period of from 4 to 20 days from inoculation.

11. The process of claim 4 in which the inoculated pulpwood is maintained under bacterial growth conditions for a period of from 4 to 20 days from inoculation.

12. The method of reducing color staining by staining fungi on structural wood cut from a log comprising inoculating exposed wood surface areas of a bark-retaining timber log with a color stain reducing effective amount of a bacterium of Pseudomonas fluorescens, allowing the bacterium to grow on and into the timber log and thereafter cutting the log into structural wood.

13. The method of claim 12 in which the log ends are inoculated.

14. The method of claim 12 in which the exposed surface areas are inoculated in no more than two weeks after cutting of the tree from which the log is obtained.

15. The method of claim 12 in which the exposed surface areas are inoculated in no more than one week after cutting of the tree from which the log is obtained.

16. The method of claim 1 in which the wood is pine wood.

17. The method of claim 12 in which a plurality of exposed wood surface areas are created by a plurality of scores lengthwise along the log and in which exposed wood surface areas from the scoring are inoculated.

18. The method of reducing color staining by staining fungi on structural wood cut from a log or on a debarked log comprising inoculating at least 50% of the surface area of the structural wood or debarked log with a color stain reducing effective amount of a bacterium of Pseudomonas fluorescens, and allowing the bacterium to grow on and into the inoculated wood.

19. The method of claim 18 in which the bacterium is inoculated onto the structural wood in no more than one week after cutting of the structural wood from its log source.

20. The method of claim 18 in which the bacterium is inoculated on the debarked log in no more than one week after the log is harvested from its tree source.

21. The method of claim 18 in which structural wood is inoculated.

22. The method of claim 18 in which a debarked log is inoculated.

23. The method of claim 22 in which the inoculation includes the ends of the log.

* * * * *